(12) United States Patent
Pham

(10) Patent No.: US 6,616,893 B1
(45) Date of Patent: Sep. 9, 2003

(54) DIAGNOSTIC TESTING KIT FOR COLLECTION AND TESTING OF FLUID SAMPLES WITH USER CONFIGURABLE TEST STRIPS AND TIMER

(76) Inventor: Tuan Pham, 9265 Activity Rd., Suite 112, San Diego, CA (US) 92126

( * ) Notice: Subject to any disclaimer, the term of this patent is extended or adjusted under 35 U.S.C. 154(b) by 0 days.

(21) Appl. No.: 09/710,734

(22) Filed: Nov. 11, 2000

Related U.S. Application Data
(60) Provisional application No. 60/165,091, filed on Nov. 12, 1999.

(51) Int. Cl.[7] ............................................. G01N 31/22
(52) U.S. Cl. .............................. 422/58; 422/50; 422/56; 422/60; 422/61; 436/164; 436/169; 436/170; 436/180
(58) Field of Search .......................... 422/61, 58, 50, 422/56, 60, 102, 57; 436/164, 169, 170, 180

(56) References Cited

U.S. PATENT DOCUMENTS

| | | | | |
|---|---|---|---|---|
| 5,656,502 A | * | 8/1997 | MacKay et al. | 436/180 |
| 5,719,034 A | * | 2/1998 | Kiser et al. | 435/14 |
| 6,379,620 B1 | * | 4/2002 | Tydings et al. | 422/58 |

* cited by examiner

Primary Examiner—Jill Warden
Assistant Examiner—Sam P. Siefke
(74) Attorney, Agent, or Firm—Donn K. Harms

(57) ABSTRACT

A diagnostic testing kit for collection of fluid samples comprising a reservoir cup insertable into a container vessel. Fluid placed in the cup is communicated to reactive test strips located in a separation cavity between the cup and the container vessel when assembled. The test strips have a reactive agent impregnated in them that reacts to specific substances in the fluid and provide a visual result through the sidewall of the container vessel to the user. An optional alarm is provided to show minimum and maximum test times.

15 Claims, 2 Drawing Sheets

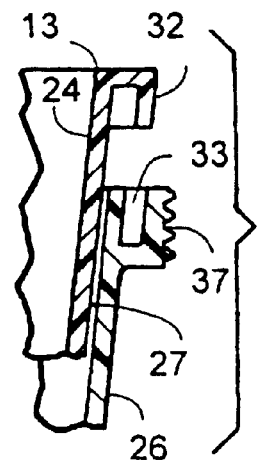
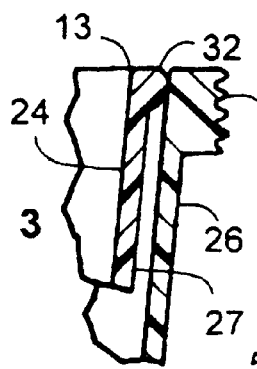
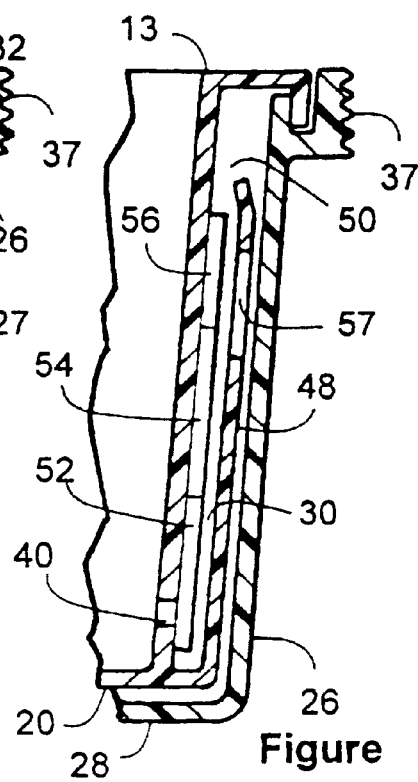
Figure 3
Figure 4
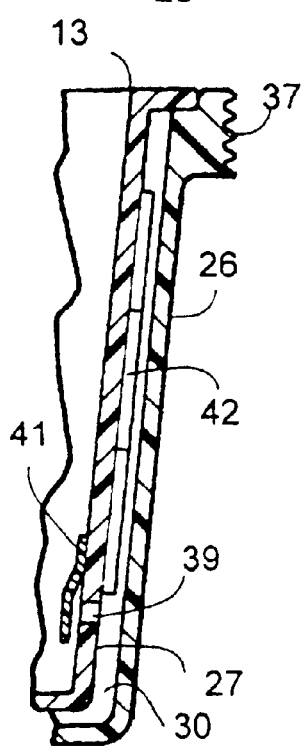
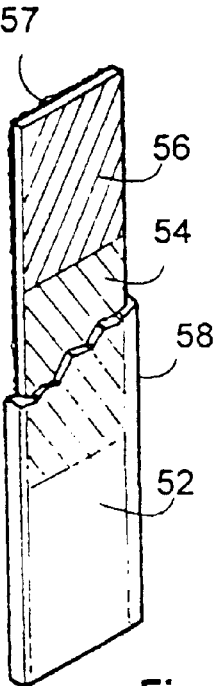
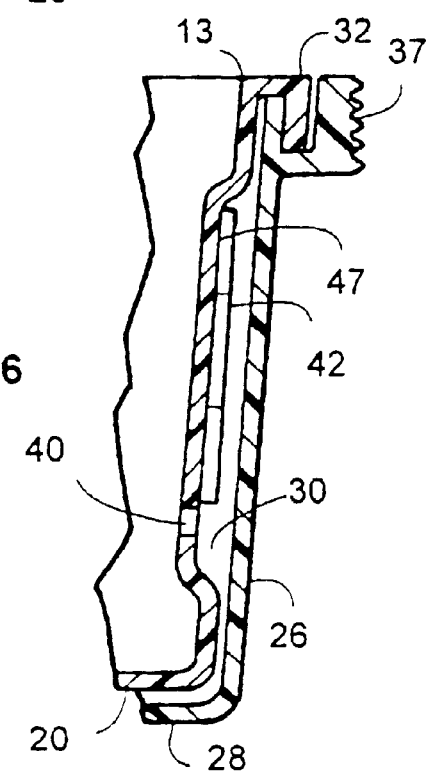
Figure 5
Figure 6
Figure 7
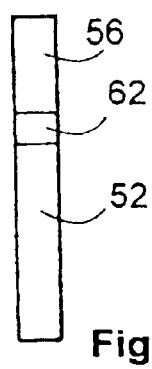
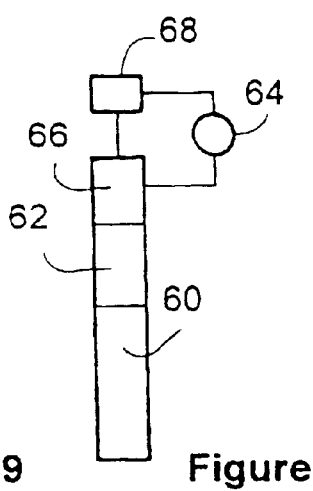
Figure 9
Figure 10
Figure 8

DIAGNOSTIC TESTING KIT FOR COLLECTION AND TESTING OF FLUID SAMPLES WITH USER CONFIGURABLE TEST STRIPS AND TIMER

This application is a continuation-in-part of copending application Ser. No. 60/165,091 filed on Nov. 12, 1999.

BACKGROUND OF INVENTION

1. Field of Invention

The present invention relates to testing of body fluids of humans and animals. More particularly it relates to test kits for diagnosis of pregnancy, drug use, or for illness of person or animal contributing the sample being tested.

2. Prior Art

Testing for pregnancy in the home and through commercial labs has long used test strips activated by certain properties of bodily fluids. Most such tests require the user to be very accurate with a fluid stream to hit a target on a small test strip. Testing using diagnostic strips that are reactive to certain chemicals, enzymes, body by products, or other fluid characteristics have also been used in recent years to diagnose illness in both humans and animals as well as to ascertain if the fluid contributor is or has recently used drugs.

In the case of pregnancy testing must such devices feature a strip held in the hand of the user who is required to urinate upon the strip and thereafter wait for some type of result yielded by the strip. Other such pregnancy testing devices require the user to place fluid into a receptacle which is then exposed to a test strip for a time period generally which the user must determine.

Drug testing in the workplace, in athletics, and by potential employers is also a common occurrence. Such testing generally requires the user to contribute a sample which is then sealed in a container and shipped to a commercial lab for the individual tests requested by the party seeking the testing of the sample. The lab then exposes the samples to the various test strips or other reactants that will provide the requested information.

As is obvious, pregnancy tests requiring a user to hit a small target with a urine stream, and then to time the reaction of the fluid with a test strip, have inherent problems. First, the fluid stream is not always accurately directed to the target thus causing problems with unintentional wetting of the user's person or other areas of the room in which the test is taking place. Second, many such tests require the user to time the contact of the test strip with the fluid collected. Should the time be miscalculated, the result can be in doubt.

Finally, the entire process is somewhat unsanitary since the user may be required to move about with urine soaked test strips or to place test strips in containers of urine or other bodily fluids and thereafter remove them after the defined time period of exposure. All of this transport and moving about risks contamination of the test being conducted as well as contact with sometimes infectious bodily fluids by the user or testing personnel performing the test.

Additional problems result in the arena of drug testing during athletic events or by employers seeking to make for a drug free workplace. In such cases the sample is generally collected, sealed, and then transported to a lab. Thereafter, the lab technicians expose the fluid sample to the appropriate reactant to determine if the contributed sample contains the marker for the drug or disease or condition for which it is being tested.

In such cases the risk of damage or contamination to the sample during transport is always a concern as is the risk of adulteration by the person being tested. Also, since currently used test strip style testing is generally not configurable on site, valuable time is lost in the transport from the site of the fluid contribution to the lab so that the test can be configured to determine if the marker in the fluid is present.

U.S. Pat. No. 5,976,895 (Cipkowski) teaches a device for collecting fluid samples and shipping them to a lab wherein a test card is inserted through a slot in the cap and read through the sidewall of the container. While Cipkowski provides for improved sanitation by the provision of a slot that cooperates with a card, the technician still must remove the cap to insert the card risking spillage and damage during transport. Also, there is no provision to time the test being conducted built into the kit thus requiring the user to time the exposure of the card and strips to the fluid.

Commercially available devices such as the TESTCUP® by Rocher Diagnostics feature easily viewed results however the device must be overturned for a defined period and then turned upright for the test to proceed. The risk of leakage of contaminated body fluids if the cap is ill fitted is ever present since the device must be overturned. Nether is the device easily configurable on site should the user wish to configure their own screening tests for certain diseases, condition, or drugs.

As such there exists a need for a device that will allow for easy placement of fluid in a container for testing. Such a device should feature viewable results without the need for insertion or removal of test strips into the container. The device should further require little or no agitation or overturning that might encourage leaking of fluids from the container. Such a device should feature a self timing mechanism to stop the reaction of fluid with the provided test strip as well an optional ability to be configurable on site by the party using the device. Still further, a timer to inform the tester of the proper time frame for the test being conducted would be desirable.

SUMMARY OF THE INVENTION

Applicant's device provides an easily manufactured and operated test kit for medical conditions of humans and animals as well as for testing of pregnancy and when properly configured for the presence of drugs. The device is a kit that allows for the placement of the body fluid to be tested inside a sealable outer container which need not be agitated or overturned to work.

The kit features an inner test cup or reservoir cup dimensioned for a cooperative engagement with a substantially transparent test container vessel. When inserted into an interior cavity formed in the container vessel the test cup which is of an outside dimension slightly smaller than the inside dimension of the interior cavity of the container vessel forms a seal with the container vessel at the open ends of both the container vessel and the reservoir test cup.

The seal formed by a sealing means such as cooperatively engageable open ends on both the container vessel and the reservoir cup prevents fluid from entering separation cavity formed between the outside of the reservoir cup wall and the inside of the container vessel wall. The cavity thus remains separated from the fluid in the reservoir cup by the sealing means and the wall of the reservoir cup.

One or a plurality of test strips are mounted to the exterior surface of the sidewall of the test cup using a means for attachment of the test strips to the wall surface such as adhesive or slots or capillaries formed into the wall surface to cooperatively engage the test strips. The strips could also be mounted on the inside wall of the container vessel but the current best mode mounts them to the reservoir cup. The test strips are thus in the separation cavity and isolated from any fluid in the reservoir cup.

Communication between the test strips and the fluid in the reservoir cup is provided by one or a plurality of apertures communicating through the sidewall of the reservoir cup. The sizing and position of the apertures thereby provide the desired communication between any fluid placed in the reservoir cup interior fluid cavity and the test strips attached to the outer wall of the reservoir cup.

By using the apertures communicating with the fluid supply and the test strips the kit is self timing in that the test strips can be configured to absorb fluid from the aperture at a desired rate by the material in the test strip as well as adjustment of the area of the apertures. Since the test strips communicate over the entire area of the apertures fluid only communicates into the test strip by absorption and is thereafter transmitted upward toward the top of the test strip by capillary action.

Once the test strip has absorbed a sufficient amount of fluid to have reached the reactant positioned at the uppermost area of the test strip from the-aperture, absorption naturally ceases since the capillary action ceases. The device is thus self timing in that it only allows a sufficient amount of fluid from the reservoir cup to reach the reactant on the test strip and then ceases the flow by ceasing the capillary action.

Additional utility may be provided by provision of the device as a kit that may be assembled by the user in a custom fashion. While the device when used for specific drug tests or pregnancy testing would probably be provided in a fashion pre configured for such testing, in the event that the user wishes to have the ability to configure the kit for varying tests, that function is also accommodated. In providing the kit in configurable fashion, a plurality of test strips would be provided to the user for the tests desired. The user can then custom configure the kit to test for the desired marker in the fluid that is inserted into the reservoir cup. This user configurability is provided by making the test strips attachable by the user as needed using adhesive or peel and stick type or by making slots or capillaries in the outer wall of the reservoir cup that would allow the user to insert the test strips therein as desire. Should a test strip not be desired in one position, a plug such as a piece of tape could be placed over the aperture to remain sealed. Such adjustability would allow users to test any one or number of drugs, conditions, or diseases, at one time and save the cost of tests that are not wanted.

Another option provided by the plurality of apertures providing contact with the fluid to be tested is the ability to place a timing means in communication with the fluid through one of the apertures that will alert the user when a time period for testing has expired. Such a timing means could be as simple as a test strip with fluid soluble ink that will move to a designated point when contacted by sufficient fluid, or a small electronic alarm that is activated by the fluid reaching a point on the upper end of a capillary style test strip.

An object of this invention is providing a kit for testing of body fluids from humans or animals that need not be overturned, shaken, or otherwise agitated to yield a result.

Another object of this invention is to provide a need for a device that will allow for easy placement of fluid in a container for testing and yield viewable test results without the need for insertion or removal of test strips into the container.

A further object of this invention is to minimize the chance of leaking of potentially dangerous fluids by minimizing handling of the device and the fluids.

An additional object of this invention is the provision of a self timing mechanism to stop the flow and reaction of fluid with test strip yielding the viewable result.

A still further object of this invention is the provision if desired of user ability to configure the kit to test for the user desired purposes on each test.

Further objects of the invention will be brought out in the following part of the specification, wherein detailed description is for the purpose of fully disclosing the invention without placing limitations thereon.

BRIEF DESCRIPTION OF DRAWING FIGURES

FIG. 3 is a cut away side view depicting the cooperative engagement of the inner reservoir cup and the container vessel to yield a seal.

FIG. 4 is cut away side view depicting another embodiment the cooperative engagement of the inner reservoir cup and the container vessel to yield a seal.

FIG. 5 is a cut away side view depicting another embodiment of the cooperative engagement of the inner reservoir cup and the container vessel to yield a seal.

FIG. 6 depicts the construction of an embodiment of the test strips for attachment to the reservoir cup.

FIG. 7 is a side cut away view of one embodiment of the device showing a twin walled reservoir cup forming capillarity passages to provide mounts for the test strips.

FIG. 8 is a side cut away view showing adhesive attachment of the test strip to the reservoir cup.

FIG. 9 depicts a timer test strip for signaling the user when a defined period of time has elapsed.

FIG. 10 depicts a timer test strip with electronic means ii for signaling the user a defined period has elapsed.

DETAILED DESCRIPTION OF THE PREFERRED EMBODIMENTS OF THE INVENTION

Figure 1:
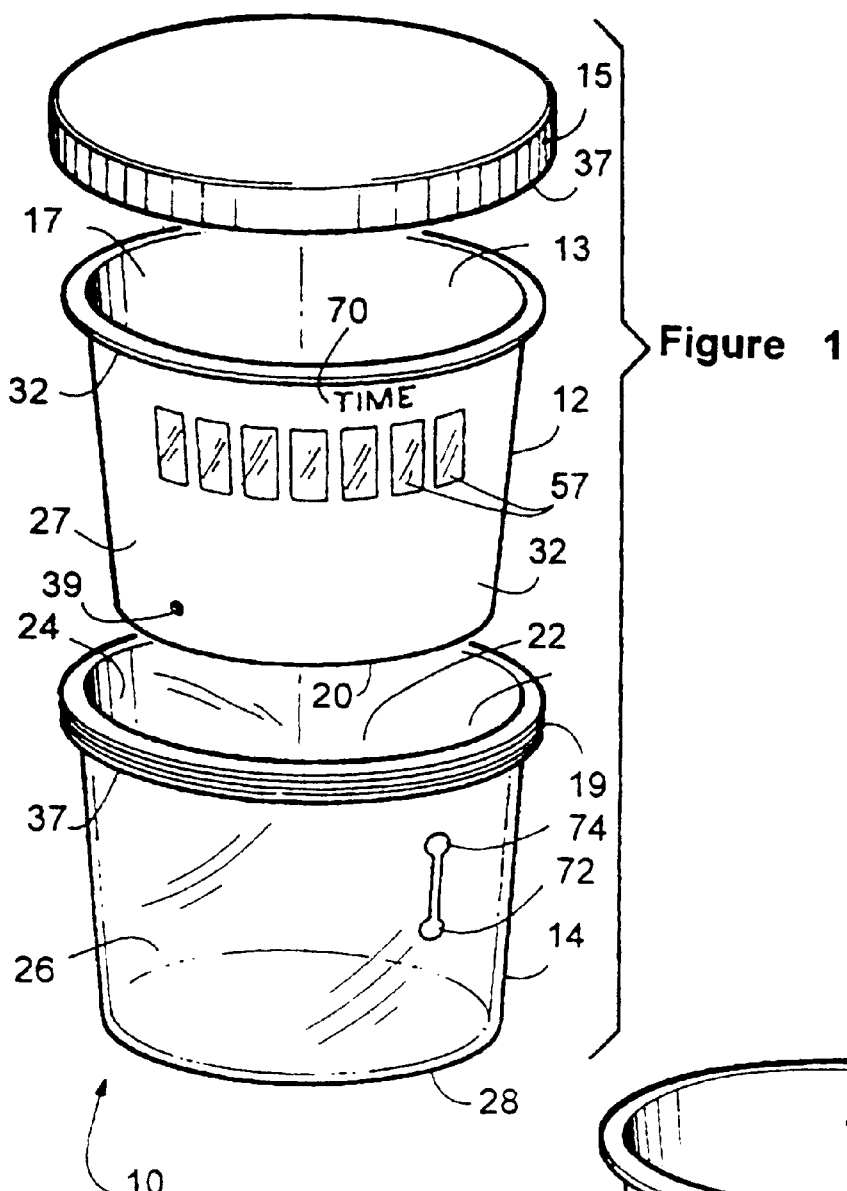
FIG. 1 is an exploded view of one embodiment of the device herein disclosed.
Figure 2:
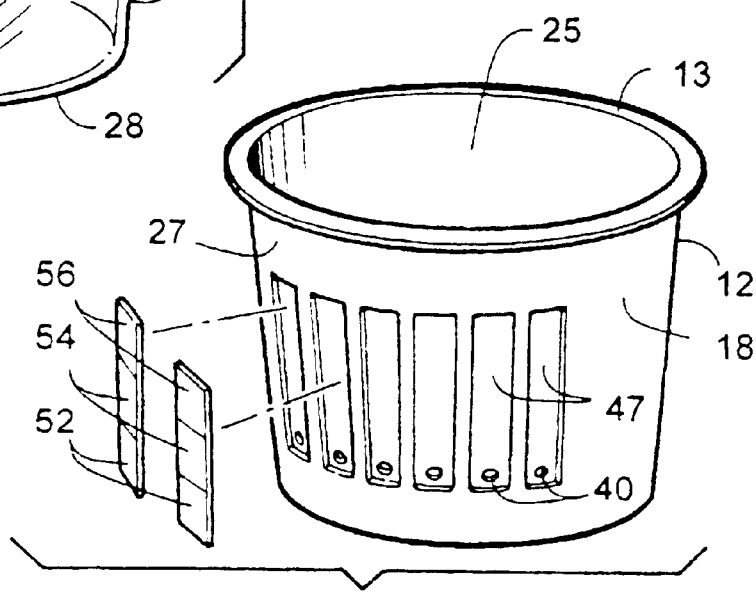
FIG. 2 is a side view of the reservoir cup and test strips and alarm for mounting thereon.

Referring now to the drawing figures which depict the preferred embodiments of the invention disclosed herein, specifically Figure which is an exploded view an embodiment of the device herein disclosed which shows the device 10 in exploded form. The device 10 is a kit of interchangeable parts that can be preassembled for sale as one unit, or can be sold in parts that may be assembled into a single operating unit to test for the feature desired in the fluid placed therein.

The device 10 features an inner reservoir cup 12 dimensioned for a cooperative sealed engagement at a top edge 13 which defines the cup aperture 17, with an upper edge 19 of the container sidewall 26 of substantially transparent test container vessel 14. When the reservoir cup 12 is configured to an assembled form of the device, the reservoir cup 12 is inserted into an interior cavity 16 formed in the container vessel 14. An interior cavity 25 of the reservoir cup 12 is defined by the area inside the container sidewall 26, the endwall 20 and the top edge 13. The reservoir cup 12 is of an outside dimension defined by the exterior surface 27 of the reservoir cup side wall 18 and reservoir cup end wall 20.

The reservoir cup 12 has dimensions smaller than container cavity 22 defined by the interior surface 24 of substantially transparent container sidewalls 26 and the container endwall 28 of the container vessel 14.

A sealing means between the reservoir cup 12 and the container vessel 14 is provided by cooperative sealed engagement of the top edge 13 and the upper edge 19 of the container vessel sidewall 26. The preferred embodiment features the cooperative engagement of the open end of the container vessel 14 at the upper edge 19 and the top edge 13 of the reservoir cup 12 using cooperatively engageable tongue 32 and groove 33 structures engageable at the open ends on both the container vessel 14 and the reservoir cup 12.

In this configuration, when the cup 12 is inserted into the container vessel 14, the cooperative sealed engagement thus forms a seal means to prevent fluid from entering separation cavity 30 formed between and defined by the outside surface 32 of the reservoir cup sidewall 18 and reservoir cup endwall 20 and the inner surface 33 of the container sidewall 26 and inner surface of container endwall 28. Of course, the sealing means might also be provided by an sealing ring 34 or lip overhang 36 on the reservoir cup 12 such that a substantially fluid tight seal is achieved between the container sidewall 26 and the reservoir cup sidewall 18 and other sealing engagements are known in the art and anticipated. By forming this seal the separation cavity 30 remains substantially fluid tight except for the fluid allowed to flow therein through apertures 40.

A cap 15 is provided to seal the device 10 prior to use from contaminants and to keep the fluid contained therein during use. The cap 15 would feature a conventional attachment to the container vessel 14 using cooperating threads 37 on both the cap 15 and the container vessel 14. Unlike other devices that require shaking, agitation, or turning upside down to function, the device 10 herein disclosed will function without the need for agitation of the fluid deposited therein.

One or a plurality of test strips 42 are positionable inside the separation cavity 30 either upon the exterior surface 44 of the sidewall 18 of the reservoir cup 12 or on the inside surface 24 of the container vessel sidewall 26 using a means for attachment of the test strips 42 in the separation cavity such as adhesive, or slots 46 dimensioned to hold the strips 42 therein. The slots 46 could be simple indents in the sidewall 18 or container sidewall 26 or could be a second sidewall 48 of the reservoir cup 12 with separations between the individual slots 46 such that individual conduits 50 formed into between the sidewall of the reservoir cup 18 and the second side wall 48. The slots 46 would thus allow for insertion of the appropriate test strip 42 into the conduit 50. In the current best mode of the device 10 at least one strip 42 is affixed to the exterior surface 21 of the reservoir cup sidewall 18. This allows for easy assembly during manufacture, or by the user to configure the device for the individual or tests intended for the device 10 by placing the appropriate test strip or strips 42 on the sidewall 18 before insertion of the reservoir cup 12 into the container vessel 14.

The test strips 42 are thus located in separate conduits 50 or just adhered separately to the exterior of the reservoir cup 12 to allow each test strip 42 communication with the fluid that is placed in the reservoir cup 12 and communicated to the separation cavity 30 thus yielding individual test results for each test strip 42 in relation to its contact with the fluid reaching the separation cavity 30. The test strips 42 in the assembled kit are also protected from contact with the fluid in the separation cavity 30 and isolated from any fluid in the reservoir cup 12 prior to the test beginning with the user depositing a specimen in the reservoir cup 12.

Means for controlled fluid flow communication of the fluid deposited in the reservoir cup 12 to the test strips 42 in the separation cavity 30 is provided in a controlled fashion by one or a plurality of apertures 40 communicating through a sidewall of the reservoir cup 12 to provide fluid to a lower end 52 of the registered test strip 42 when attached to the reservoir cup 12 exterior or the interior of the container vessel 14 inside the separation cavity 30. In current preferred mode of controlled fluid communication the apertures 40 are dimensioned to communicate a defined amount of fluid placed in the reservoir cup 12 through the sidewall 18 to the lower portion 52 of the test strip 42 which covers the entire area of the aperture 40 when properly mounted to the reservoir cup 12. The sizing and position of the apertures 40 thereby provides the desired communication between any fluid placed in the reservoir cup 12 interior fluid cavity 21 and the test strips attached to the outer wall of the reservoir cup 12, while the test strips 42 and aperture 40 size concurrently control the flow of the fluid through the apertures 40 when mounted on the reservoir cup 12 sidewall 18 with the lower end 52 completely covering the aperture 40.

An additional means for controlled fluid flow communication of the specimen fluid in the reservoir cup 12 to the test strip 42 in the separation chamber 30 would be a narrowing of the diameter of the endwall 20 of the reservoir cup 12 to yield an inward taper of the sidewall 18 of the reservoir cup 12. The result would be that the separation cavity would be larger at the bottom end due to increased spacing between the reservoir sidewall 18 and the container vessel sidewall 26. This would slow the flow of fluid to the strip 42 by requiring longer time periods to fill the bottom of the separation cavity 30 through passage 39 to reach the strips 42. Of course the flow could be controlled to make it faster or slower by enlarging the diameter of the cup endwall 20 to narrow the separation cavity 30 or increasing the passage 39 size to increase flow, or combinations thereof.

Another means for controlled fluid flow communication of specimen fluid deposited in the reservoir cup 12 to the test strip 42 in the separation cavity 30 may be one or a plurality of passages 39 communicating through the reservoir cup sidewall 18 to the separation cavity 30 whereby the bottom of the separation cavity 30 fills with fluid which contacts the test strip 42. The rate of fluid flow may be controlled by changing the size of the passages 39 or placing a flapper valve 41 over the passages 39 to control flow therethrough.

An additional preferred manner of providing a means for controlled fluid flow communication by using the apertures 40 to communicate the fluid supply in the reservoir cup 12 with the lower end 52 of the test strips 42, the kit device 10 is self timing for final results. In this embodiment the test strips 42 are configured to absorb fluid from the aperture adjacent to them at a desired rate by the material used at the lower end of the test strip 42 as well as adjustment of the area of the apertures 40. A larger aperture 40 yields more flow of fluid in the cup 12 to the test strip 42. Since the lower end 52 of the test strips communicate over the entire area of the apertures 40, fluid only communicates into the separation cavity 30 by absorption into the lower end of the test strip 42 with the fluid thereafter transmitted upward toward a middle portion 54 and top portion 56 of the test strip 42 by capillary action. A clear coating 58 may also be added to one side of the test strip 42 to insure no leakage of fluid from the test strip 42 when fluid is being drawn upward therein.

Once the test strip 42 has absorbed a sufficient amount of fluid communicated from the reservoir cup cavity 21 to the separation cavity 30 where the fluid has reached the reactive agent positioned at the uppermost area 56 of the test strip 42 from the aperture 40, absorption of fluid naturally ceases since the capillary action ceases. The device 10 is thus self measuring as to the quantity of fluid exposed to the reactant in the top portion 56 in that it only allows a sufficient amount of fluid from the reservoir cup 12 communicated to the separation cavity 30 to reach the reactant in the top portion 56 of the test strip 42 and then ceases the flow by ceasing the capillary action.

The reactant used in the top portion can be one of enzymes or chemicals that are conventionally used to determine if a specific chemical or drug is present in the fluid sample, or to determine a specific health condition of the sample donor, such as pregnancy. As a general rule, such reactive agents visually provide a positive reaction for a specific substance or marker that is in the fluid sample that would identify the chemical, drug, or health condition being tested. A change of color, or other visual change of appearance, of the upper portion 56 of test strip 42 where the reactant is impregnated, thereby provides a visual confirmation of the test results when viewed through the substantially transparent container sidewalls 26. The user can thus pour the liquid to be tested into the reservoir cup 12 and thereby allow the fluid to communicate to the lower end 52 of the test strip 12 through the apertures 40. The fluid will thereafter be drawn upward in the test strip by capillary action of the fabric of the test strip and contact the reactant which has been impregnated or otherwise placed in the uppermost portion 56 of the test strip 42. After a defined period of time the reactant will visually confirm the presence of the substance being tested for, or the lack of the substance by a change of appearance or failure to change appearance as the case may be.

The reactant means may be one that shows pregnancy when the body fluid reacts thereto or a reactant that shows the presence of drugs in the system of the fluid donor. Alternatively a plurality of test strips 42 can be provided with a plurality of different reactant agents that will identify any of a plurality of desired substances in the fluid that is placed in the cup 12. The device can thus be used as a pregnancy test, a drug test, or a test for other biological conditions where a reactant can be placed in the test strip 12.

Additional utility in showing results can be by the provision of viewing windows 57 either formed in the sidewall of the cup 12 or printed on the container vessel sidewall 26 through which the upper portion 56 of the test strip can be seen. The reactant in this portion if it reacts to a positive test by changing to one or a number of colors would show through the window 57 and allows indicia 70 to be placed adjacent thereto to aid in identifying the test result.

By providing the device 10 to institutional users in disassembled kit form, additional utility to such users may be provided. The device 10 in kit form would be provided in pieces to be assembled as needed. Different types of test strips 42 with different reactant agents thereon to identify different drugs or physical conditions would also be provided. The user would therein assemble the device 10 using the type of test strip 42 which carries the reactant to identify the fluid characteristic desired for the drug or physical characteristic being tested.

In the event that adulterant prevention or other confirmable test tracking is required to insure that nothing has been added to the specimen deposited into the interior cavity 25 or the reservoir cut 12, the device may be provided with optional means to seal the cavity 25 prior to use. In the current best mode a membrane 50 would be affixed to the top edge 13 of the reservoir cup 12 and would then be cut away just prior to use. Other manner of such control is known and anticipated.

While the device when used for specific drug tests or in pregnancy testing and sold at retail outlets would best be provided in a fashion pre configured for such testing, in the event that the user wishes to have the ability to configure the kit for varying tests, that function is also accommodated by the disassembled embodiment of the device that may be user assembled. This user configurability is provided by making the test strips 42 attachable by the user in the separation cavity 30 as needed, using adhesive or peel and stick type or by providing slots 46 or capillaries in the outer wall of the reservoir cup 12 or on the inner surface 24 of the separation cavity 30 that would allow the user to insert the test strips 42 therein as desire. Should a test strip not be desired in one position a plug such as a piece of tape could be placed over the aperture to remain sealed. Such adjustability as to the type and number of test strips 42 would allow users to test of any one or number of drugs, conditions, or diseases, at one time and save the cost of tests that are not wanted.

Another option is the ability to place a timing means in communication with the fluid reaching the separation cavity 30. Such a timing means in the current best mode will alert the user when a determined time period required for testing has been reached or has expired. Such a timing means could be as simple as a timing test strip 61 with a fluid soluble ink 62 thereon placed in the strip material at a middle portion 52 that will naturally move upward when dissolved by the fluid during capillary action to a designated section 56 to show proper time for the test required has elapsed by colorizing the designated section 56. In some cases where strict timing between a maximum and minimum time is required, the continued colorizing to the upper potion 57 of the designated section 56 will thus signal to the user the test is now invalid as timing parameters have expired. This signal would be visual and viewed through the container sidewall 26 which could also be marked with a scale or signal through which the colorization of the designated point 56 is viewed.

When contacted by sufficient fluid to reach a designated point for determined minimum test time 55 the designated section 56 would change color to signal the time was up and would be viewed using a first timing point designation 72 that can be printed on the sidewall 18 or alternately on the cup 12, to register at the proper timing position with the strip 61. If a maximum determined test time signal is required for the test being conducted, a second point or determined maximum time point 74 would be designated on the sidewall 18 or possibly on the cup 12 to show that time parameters have been exceeded.

In the alternative the timing means could also be a small electronic alarm 64 that is activated by the fluid reaching the upper point of a timing style test strip 61 and activating a fluid activated switch 66 when fluid reaches that point at a determined time which would connect battery 68 power to the alarm means 64 thereby visually or audibly alerting the user. One or a combination of a group consisting of a light bulb, a light emitting diode or an audible alarm would work well as the signaling part of the alarm means. The alarm means 64 could have an electronic timer built in to stop or change the alarm to show that the determined maximum time has been reached should that be required.

In the event that more information is desired by users of the device as to the results of the tests, and in the case of the maximum and minimum time point designations, indicia 70 may be placed on one or both of the exterior of the reservoir cup 12 or the sidewalls 26 of the container vessel 14 to identify the test, the results, or other information desired by the user. Further, the audible alarm portion of the alarm means 64, using conventional electronic memory and playback processing such as that used in novelty "talking" greeting cards, could announce the results of a positive test for pregnancy to the user in an audible fashion. This might be especially helpful for visually challenged users, or users who cannot read indicia to determine the results obtained.

While all of the fundamental characteristics and features of the Diagnostic testing kit for collection and testing of fluid samples with user configurable test strips and timer have been shown and described, it should be understood that various substitutions, modifications, and variations may be made by those skilled in the art without departing from the spirit or scope of the invention. Consequently, all such modifications and variations are included within the scope of the invention.

What is claimed is:

1. A diagnostic testing kit for collection of fluid samples comprising:

a reservoir cup, said reservoir cup having a cup sidewall communicating at a bottom end with a reservoir endwall;

a top edge of said reservoir cup at the upper portion of said cup sidewall opposite said bottom end, said top edge defining a reservoir aperture;

an interior cavity of said reservoir cup, said interior cavity defined by said reservoir side wall, said reservoir endwall, and said top edge;

a container vessel, said container vessel having a container sidewall communicating at a.bottom portion with a container endwall;

an upper edge of said container sidewall opposite said bottom portion said upper edge defining a container aperture;

a container cavity defined by said container sidewall, said container endwall, and said upper edge;

means for sealed cooperative engagement of said top edge with said upper edge;

a separation cavity defined by area between the exterior surface of said reservoir side wall and said reservoir endwall and the surface area of said container cavity when said top edge is cooperatively engaged with said upper edge;

at least one test strip located in said separation cavity, said test strip having a bottom portion adjacent to said reservoir endwall, said bottom portion in direct communication with liquid deposited in said interior cavity, said bottom portion capable of communication of liquid communicated thereto to a top portion of said test strip, said top portion having a reactant end adjacent to said upper edge containing a reactive agent which visually reacts to specific contents in said fluid communicated thereto, thereby providing a test result which may be viewed through the container sidewall; and means to communicate the flow rate of a liquid specimen deposited in said interior cavity to said bottom portion of said test strip in said separation cavity, whereby body fluid deposited in said interior cavity is communicated directly to said bottom portion of said test strip in said separation cavity at a controlled flow rate and said test strip thereafter displays said test result.

2. The diagnostic testing kit for collection of fluid samples as defined in claim 1 further comprising:

a timing means located in said separation cavity, said timing means providing a signal when sufficient time has elapsed to render said test result valid.

3. The diagnostic testing kit for collection of fluid samples as defined in claim 1 further comprising:

a cap, said cap cooperatively engageable with one of said upper edge or said top edge.

4. The diagnostic testing kit for collection of fluid samples as defined in claim 1 wherein said at least one test strip is located in said separation cavity by affixation to said exterior surface of said receiver cup sidewall.

5. The diagnostic testing kit for collection of fluid samples as defined in claim 1 wherein said at least one test strip is located in said separation cavity by affixation to said container vessel sidewall.

6. The diagnostic testing kit for collection of fluid samples as defined in claim 1 wherein said means to communicate the flow rate of a liquid specimen deposited in said interior cavity to to said bottom portion of said test strip in said separation cavity is at least one aperture communicating between through said reservoir sidewall.

7. The diagnostic testing kit for collection of fluid samples as defined in claim 4 wherein said means to communicate the flow rate of a liquid specimen deposited in said interior cavity to to said bottom portion of said test strip in said separation cavity is at least one aperture communicating between through said reservoir sidewall.

8. The diagnostic testing kit for collection of fluid samples as defined in claim 7 further comprising:

a timing means located in said separation cavity, said timing means communicating with said fluid communicated to said separation cavity and reacting thereto over a defined period of time to provide a signal to the user when sufficient time has elapsed to render said test result valid.

9. The diagnostic testing kit for collection of fluid samples as defined in claim 8 wherein said signal is visually observable through the container vessel sidewall.

10. The diagnostic testing kit for collection of fluid samples as defined in claim 8 wherein said signal is visually observable through the container vessel sidewall and includes a maximum time allowed signal also visible through said container vessel sidewall.

11. The diagnostic testing kit for collection of fluid samples as defined in claim 6 further comprising a valve means controlling fluid flow through said aperture.

12. The diagnostic testing kit for collection of fluid samples as defined in claim 7 further comprising a valve means controlling fluid flow through said aperture.

13. The diagnostic testing kit for collection of fluid samples as defined in claim 9 wherein said alarm is color change in said test strip.

14. The diagnostic testing kit for collection of fluid samples as defined in claim 9 wherein said alarm is a light source activated after a defined time of contact with said fluid.

15. The diagnostic testing kit for collection of fluid samples as defined in claim 1 wherein said means to communicate the flow rate of a liquid specimen deposited in said interior cavity to said bottom portion of said test strip in said separation cavity is provided by a narrowing of the bottom end of said reservoir cup with widens the bottom end of said interior cavity.

\* \* \* \* \*